(12) United States Patent
Park et al.

(10) Patent No.: US 12,102,465 B2
(45) Date of Patent: Oct. 1, 2024

(54) THREE-DIMENSIONAL SCANNER AND SCANNING METHOD USING SAME (71) Applicant: DOF INC., Seoul (KR)

(72) Inventors: Hyunsoo Park, Seoul (KR); Heungsik Sim, Suwon-si (KR)

(73) Assignee: DOF INC., Seoul (KR)

( * ) Notice: Subject to any disclaimer, the term of this patent is extended or adjusted under 35 U.S.C. 154(b) by 563 days.

(21) Appl. No.: 17/414,931

(22) PCT Filed: Dec. 17, 2019

(86) PCT No.: PCT/KR2019/017922
§ 371 (c)(1),
(2) Date: Jun. 16, 2021

(87) PCT Pub. No.: WO2020/130598
PCT Pub. Date: Jun. 25, 2020

(65) Prior Publication Data
US 2022/0061786 A1    Mar. 3, 2022

(30) Foreign Application Priority Data

Dec. 21, 2018 (KR) .......................... 10-2018-0167837

(51) Int. Cl.
*A61B 6/14* (2006.01)
*A61B 5/00* (2006.01)
(Continued)

(52) U.S. Cl.
CPC ............ *A61B 6/512* (2024.01); *A61B 5/0062* (2013.01); *A61B 5/0088* (2013.01); *A61C 9/0053* (2013.01); *A61C 9/006* (2013.01)

(58) Field of Classification Search
None
See application file for complete search history.

(56) References Cited

U.S. PATENT DOCUMENTS 9,752,867 B2 * 9/2017 Atiya ................... A61B 5/1079
2004/0141336 A1 * 7/2004 West ..................... A61C 19/004
362/555

(Continued)

FOREIGN PATENT DOCUMENTS

JP    2012-045346 A    3/2012
JP    2017-113389 A    6/2017
(Continued)

OTHER PUBLICATIONS

International Search Report in International Application No. PCT/KR2019/017922, dated Mar. 27, 2020, 2pages.

*Primary Examiner* — Mohammad J Rahman
(74) *Attorney, Agent, or Firm* — Park, Kim & Suh, LLC (57) ABSTRACT

The present invention relates to a three-dimensional intraoral scanner and an intraoral scanning method using same, the scanner being capable of reducing a matching error generated during a three-dimensional model data generation process for all the teeth in an oral cavity, and the three-dimensional intraoral scanner and the intraoral scanning method using same, according to one embodiment of the present invention, generate three-dimensional model data for all the teeth in an oral cavity by using a large-area scan image, thereby enabling the minimization of cumulative errors generated when the three-dimensional scan data is matched, and match, with the three-dimensional model data, three-dimensional scan data generated by using a narrow-area two-dimensional scan image, thereby enabling improved precision of the three-dimensional model data.

12 Claims, 9 Drawing Sheets

(51) Int. Cl.
*A61B 6/51* (2024.01)
*A61C 9/00* (2006.01)

(56) References Cited

U.S. PATENT DOCUMENTS

| | | | | |
|---|---|---|---|---|
| 2004/0218039 | A1* | 11/2004 | Cooper | A61B 1/05 348/66 |
| 2004/0254476 | A1* | 12/2004 | Quadling | G01B 11/24 356/601 |
| 2006/0001739 | A1* | 1/2006 | Babayoff | A61B 5/1077 348/E13.005 |
| 2012/0092461 | A1* | 4/2012 | Fisker | A61B 5/1077 348/46 |
| 2014/0146142 | A1* | 5/2014 | Duret | A61C 19/04 348/46 |
| 2016/0012182 | A1* | 1/2016 | Golay | G16H 40/20 705/3 |
| 2016/0256244 | A1* | 9/2016 | Babayoff | A61B 1/253 |
| 2016/0338803 | A1* | 11/2016 | Pesach | G06T 7/74 |
| 2017/0181815 | A1* | 6/2017 | Pulido | A61C 9/0053 |
| 2017/0215698 | A1* | 8/2017 | Rynerson | A61B 1/00048 |
| 2018/0027159 | A1* | 1/2018 | Dillon | A61B 5/0088 348/66 |
| 2018/0028063 | A1* | 2/2018 | Elbaz | A61B 5/7435 |
| 2019/0029522 | A1* | 1/2019 | Sato | A61C 7/10 |
| 2019/0070064 | A1* | 3/2019 | Hogle | G06V 10/44 |
| 2019/0094981 | A1* | 3/2019 | Bradski | G06F 3/0346 |
| 2019/0129159 | A1* | 5/2019 | Dickensheets | G02B 21/361 |
| 2019/0192262 | A1* | 6/2019 | Pesach | G06T 15/60 |
| 2019/0328489 | A1* | 10/2019 | Capron-Richard | A61B 6/5247 |
| 2020/0020165 | A1* | 1/2020 | Tran | G06F 3/011 |
| 2021/0169318 | A1* | 6/2021 | Sorimoto | G02B 21/22 |

FOREIGN PATENT DOCUMENTS

| | | |
|---|---|---|
| JP | 2018-171323 A | 11/2018 |
| KR | 10-1911327 B1 | 10/2018 |
| KR | 10-2018-0118882 A | 11/2018 |
| KR | 10-2018-0128589 A | 12/2018 |

\* cited by examiner

THREE-DIMENSIONAL SCANNER AND SCANNING METHOD USING SAME

CROSS-REFERENCE TO RELATED APPLICATIONS

This application is the National Stage filing under 35 U.S.C. 371 of International Application No. PCT/KR2019/017922, filed on Dec. 17, 2019, which claims the benefit of Korean Patent Application No. 10-2018-0167837, filed on Dec. 21, 2018, the contents of which are all hereby incorporated by reference herein in their entirety.

FIELD OF INVENTION

The present disclosure relates to a three-dimensional (3D) intraoral scanner and an oral cavity scanning method using the same, and more particularly to a 3D intraoral scanner and an oral cavity scanning method using the same for reducing a registration error occurring in a procedure of generating 3D model data of all the teeth in the oral cavity.

BACKGROUND OF INVENTION

A three-dimensional (3D) intraoral scanner is an optical device that is inserted into an oral cavity of a dental patient and scans the teeth in a non-contact manner to generate 3D model data for all teeth in the oral cavity, and thus, it is possible to easily and conveniently take an impression of a patient in a short period of time and is widely used in dentistry recently.

An active method, which is an example of a method of obtaining a scanned image using a 3D intraoral scanner, is a method of irradiating a tooth surface with known patterned light, acquiring a plurality of optical images by photographing an irradiated pattern using an optical camera, and then acquiring 3D scan data using triangulation.

Since the 3D intraoral scanner is capable of scanning only a visible part, it is impossible to scan all teeth in the oral cavity at once, and thus, in order to generate 3D model data of all teeth in the oral cavity, 3D scan data is generated by scanning areas divided from the oral cavity and the 3D scan data are registered for several areas generated through the scan, thereby acquiring the 3D model data of all teeth in the oral cavity.

However, since an error occurs when 3D scan data are registered, if 3D scan data for several areas are registered to obtain 3D model data for all teeth in the oral cavity, there is a problem in that 3D scan data different from all teeth in the oral cavity of a patient are generated while errors are accumulated every time the 3D scan data are registered.

Therefore, in order to reduce the cumulative error when 3D scan data are registered, it is necessary to reduce the number of 3D scan data to be registered to obtain 3D model data for all teeth in the oral cavity.

In particular, since a conventional 3D intraoral scanner acquires a scan image of the teeth in the oral cavity using a reflector in which a scan area is inevitably narrow, the number of 3D scan data to be registered to obtain 3D model data for all teeth in the oral cavity is inevitably increased, and accordingly, in the case of a conventional three-dimensional intraoral scanner, there is a problem in that there is a limit in reducing the accumulated errors occurring when the 3D scan data are registered.

As the prior art to overcome the problems, Korean Patent Publication No. 10-1911327 (published on 25 Oct. 2018) discloses "Oral scanning method for reducing cumulative registration error, intraoral scanner, and recording medium recording a program for executing method", but the prior art has a problem in that a wide-angle camera for acquiring an image of the entire tooth area in the oral cavity in addition to a scanning camera, thereby increasing manufacturing cost.

SUMMARY OF INVENTION

Technical Problem to be Solved

To overcome the above problems, the present disclosure may provide a three-dimensional (3D) intraoral scanner and an oral cavity scanning method using the same for reducing a registration error occurring in a procedure of generating 3D model data of all the teeth in the oral cavity.

Technical Solution

According to an embodiment of the present disclosure, a three-dimensional (3D) intraoral scanner includes a case having a front surface including a light outlet and a light inlet, a light output unit disposed in the case and configured to output light into an oral cavity through the light outlet, an image sensing unit disposed in the case and configured to acquire 2D scan image of a tooth in the oral cavity from reflected light incident through the light inlet, and a reflector member detachably installed on the case and including a reflector configured to reflect light output through the light outlet into the oral cavity and to reflect reflected light reflected from the oral cavity to the light inlet when installed in the case, wherein, if the 2D scan image acquired from the reflected light, reflected by the reflector, by the image sensing unit when the reflector member is installed on the case is referred to as 2D scan image of a narrow area and 2D scan image that is acquired from entire reflected light incident through the light inlet by the image sensing unit in a state in which the reflector member is not installed on the case is referred to as 2D scan image of a wide area, the 2D scan image that is acquired from the entire reflected light incident through the light inlet by the image sensing unit in a state in which the reflector member is installed on the case is the 2D scan image of the wide area including the 2D scan image of the narrow area.

According to an embodiment of the present disclosure, the 3D intraoral scanner may include a detector configured to detect whether the reflector member is installed, and a 3D scan data generator configured to generate 3D scan data of the tooth in the oral cavity using the 2D scan image of the wide area when installation of the reflector member is not detected by the detector, and to generate the 3D scan data of the tooth in the oral cavity using the 2D scan image of the narrow area when installation of the reflector member is detected by the detector.

According to an embodiment of the present disclosure, if the 3D scan data of the tooth in the oral cavity, generated using the 2D scan image of the wide area by the 3D scan data generator, is referred to as 3D scan data of a wide area, and the 3D scan data of the tooth in the oral cavity, generated using the 2D scan image of the narrow area, is referred to as 3D scan data of a narrow area, the 3D intraoral scanner may include a 3D model data generator configured to generate 3D model data of all teeth in the oral cavity by registering the 3D scan data of the wide area and to register the 3D scan data of the narrow area to the 3D model data.

According to an embodiment of the present disclosure, the 3D intraoral scanner may include a detector configured to detect whether the reflector member is installed, and a controller configured to control the light output unit to output light output through the light outlet only to the reflector when installation of the reflector member is detected by the detector.

In the 3D intraoral scanner according to an embodiment of the present disclosure, the reflector member may include at least one of a primary light unit hiding a part of the light outlet to output only the light output to the reflector of the light output through the light outlet when installed on the case, and a secondary light unit hiding a part of the light inlet to allow only reflected light reflected by the reflector of the reflected light incident through the light inlet to be incident.

In the 3D intraoral scanner according to an embodiment of the present disclosure, the reflector member may be rotatably installed on the case.

In the 3D intraoral scanner according to an embodiment of the present disclosure, the reflector member may include a coupler detachably installed on the front surface of the case, and an extension extending from one side of the coupler and having an end with the reflector.

According to an embodiment of the present disclosure, a three-dimensional (3D) intraoral scanner may include a case having a front surface including a light outlet and a light inlet, a light output unit disposed in the case and configured to output light into an oral cavity through the light outlet, an image sensing unit disposed in the case and configured to acquire 2D scan image of a tooth in the oral cavity from reflected light incident through the light inlet, a reflector member detachably installed on the case and including a reflector configured to reflect light output through the light outlet into the oral cavity and to reflect reflected light reflected from the oral cavity to the light inlet when installed in the case, a detector configured to detect whether the reflector member is installed, and a 3D scan data generator configured to generate 3D scan data of the tooth in the oral cavity using the 2D scan image acquired by the image sensing unit, wherein, if the 2D scan image acquired from the reflected light, reflected by the reflector, by the image sensing unit when the reflector member is installed on the case is referred to as 2D scan image of a narrow area and 2D scan image that is acquired from entire reflected light incident through the light inlet by the image sensing unit in a state in which the reflector member is not installed on the case is referred to as 2D scan image of a wide area, the 3D scan data generator generates 3D scan data of the tooth in the oral cavity using the 2D scan image of the wide area when installation of the reflector member is not detected by the detector, and generates the 3D scan data of the tooth in the oral cavity using the 2D scan image of the narrow area when installation of the reflector member is detected by the detector.

In the 3D intraoral scanner according to an embodiment of the present disclosure, if the 3D scan data of the tooth in the oral cavity, generated using the 2D scan image of the wide area by the 3D scan data generator, is referred to as 3D scan data of a wide area, and the 3D scan data of the tooth in the oral cavity, generated using the 2D scan image of the narrow area, is referred to as 3D scan data of a narrow area, the 3D intraoral scanner may include a 3D model data generator configured to generate 3D model data of all teeth in the oral cavity by registering the 3D scan data of the wide area and to register the 3D scan data of the narrow area to the 3D model data.

According to an embodiment of the present disclosure, a three-dimensional (3D) intraoral scanner may include a case having a front surface including a light outlet and a light inlet, a light output unit disposed in the case and configured to output light into an oral cavity through the light outlet, an image sensing unit disposed in the case and configured to acquire a 2D scan image of a tooth in the oral cavity from reflected light incident through the light inlet, a reflector member detachably installed on the case and including a reflector configured to reflect light output through the light outlet into the oral cavity and to reflect reflected light reflected from the oral cavity to the light inlet when installed in the case, a 3D scan data generator configured to generate 3D scan data of the tooth in the oral cavity using 2D scan image acquired in a state in which the reflector member is not installed, and generates 3D scan data of the tooth in the oral cavity using 2D scan image acquired from the reflected light reflected from the reflector when the reflector member is installed, and a 3D model data generator configured to generate 3D model data of all teeth in the oral cavity by registering the 3D scan data generated in the state in which the reflector member is not installed and to register the 3D scan data generated when the reflector member is installed to the 3D model data.

According to an embodiment of the present disclosure, a three-dimensional (3D) intraoral scanner may include a case having a front surface including a light outlet and a light inlet, a light output unit disposed in the case and configured to output light into an oral cavity through the light outlet, an image sensing unit disposed in the case and configured to acquire 2D scan image of a tooth in the oral cavity from reflected light incident through the light inlet, a reflector member detachably installed on the case and including a reflector configured to reflect light output through the light outlet into the oral cavity and to reflect reflected light reflected from the oral cavity to the light inlet when installed in the case, a detector configured to detect whether the reflector member is installed, and a controller configured to control the light output unit to output light output through the light outlet only to the reflector when installation of the reflector member is detected by the detector.

According to an embodiment of the present disclosure, a three-dimensional (3D) intraoral scanner may include a case having a front surface including a light outlet and a light inlet, a light output unit disposed in the case and configured to output light into an oral cavity through the light outlet, an image sensing unit disposed in the case and configured to acquire 2D scan image of a tooth in the oral cavity from reflected light incident through the light inlet, a reflector member detachably installed on the case and including a reflector configured to reflect light output through the light outlet into the oral cavity and to reflect reflected light reflected from the oral cavity to the light inlet when installed in the case, a detector configured to detect whether the reflector member is installed, and a 3D scan data generator configured to generate 3D scan data of the tooth in the oral cavity using the 2D scan image acquired by the image sensing unit, wherein the reflector member includes a coupler detachably installed on the front surface of the case, and an extension extending from one side of the coupler and having an end with the reflector.

In the 3D intraoral scanner according to an embodiment of the present disclosure, the reflector member may include at least one of a primary light unit hiding a part of the light outlet to output only the light output to the reflector of the light output through the light outlet when installed on the case, and a secondary light unit hiding a part of the light inlet to allow only reflected light reflected by the reflector of the reflected light incident through the light inlet to be incident.

According to an embodiment of the present disclosure, an oral cavity scanning method using a three-dimensional (3D) intraoral scanner including a case having a front surface including a light outlet and a light inlet, a light output unit configured to output light into an oral cavity through the light outlet, an image sensing unit configured to acquire 2D scan image of a tooth in the oral cavity from reflected light incident through the light inlet, and a reflector member detachably installed on the case and including a reflector configured to reflect light output through the light outlet into the oral cavity and to reflect reflected light reflected from the oral cavity to the light inlet when installed in the case includes, if the 2D scan image acquired from the reflected light, reflected by the reflector, by the image sensing unit is referred to as 2D scan image of a narrow area and 2D scan image that is acquired from entire reflected light incident through the light inlet by the image sensing unit in a state in which the reflector member is not installed is referred to as 2D scan image of a wide area, acquiring the 2D scan image of the wide area in a state in which the reflector member is not installed on the case, generating 3D scan data of a wide area of the tooth in the oral cavity using the acquired 2D scan image of the wide area, generating 3D model data of all teeth in the oral cavity by registering the 3D scan data of the wide area, acquiring the 2D scan image of the narrow in a state in which the reflector member is installed on the case, generating 3D scan data of a narrow area of the tooth in the oral cavity using the acquired 2D scan image of the narrow area, and registering the 3D scan data of the narrow area to the 3D model data.

In the method according to an embodiment of the present disclosure, the 2D scan image that is acquired from the entire reflected light incident through the light inlet by the image sensing unit in a state in which the reflector member is installed on the case may be the 2D scan image of the wide area including the 2D scan image of the narrow area, and the acquiring the 2D scan image of the narrow area may include acquiring the 2D scan image of the wide area in a state in which the reflector member is installed on the case, and selecting the 2D scan image of the narrow area from the 2D scan image of the wide area.

Effect of Invention

By virtue of a three-dimensional (3D) intraoral scanner 10 and the oral cavity scanning method S10 using the same according to an embodiment of the present disclosure as configured above, the 3D model data of all the teeth in the oral cavity may be generated using a scan image of a wide area, and thus accumulated errors occurring when 3D scan data is registered may be minimized, and the 3D scan data generated using the 2D scan image of the narrow area may be registered to the 3D model data, thereby improving precision of the 3D model data.

It will be appreciated by persons skilled in the art that the effects that could be achieved with the present disclosure are not limited to what has been particularly described hereinabove and other advantages of the present disclosure will be more clearly understood from the above detailed description.

BRIEF DESCRIPTION OF DRAWINGS

FIGS. 1 and 2 are schematic diagrams of a three-dimensional (3D) intraoral scanner according to an embodiment of the present disclosure.

BEST MODE

Hereinafter, the present disclosure will be described in detail. In the description with reference to the accompanying drawings, the same components are given the same reference numerals, and repeated description thereof will be omitted.

Terms such as first and second may be used to describe components, but the components are not limited to the above terms, and are used only for the purpose of distinguishing one component from other components.

When a part "includes" a certain component, it means that other components are further included, rather than excluding other components, unless otherwise stated.

In the drawings, the thickness or size of each layer (film), region, pattern or structure may be changed for clarity and convenience of description, and thus does not fully reflect the actual size.

In addition, each embodiment may be implemented independently or together, and some components may be excluded in accordance with the purpose of the invention.

Figure 1:
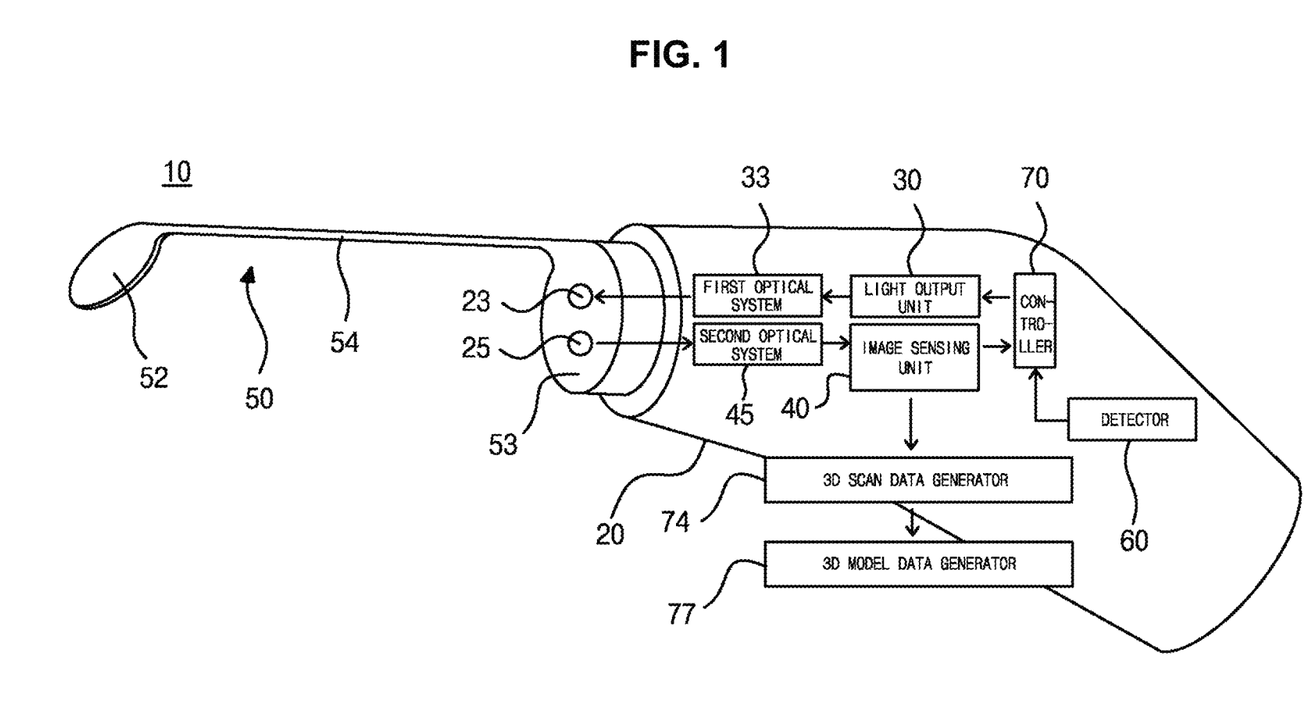
FIG. 1 is a diagram showing the state in which a reflector member is coupled to a case of a 3D intraoral scanner according to an embodiment of the present disclosure.
Figure 2:
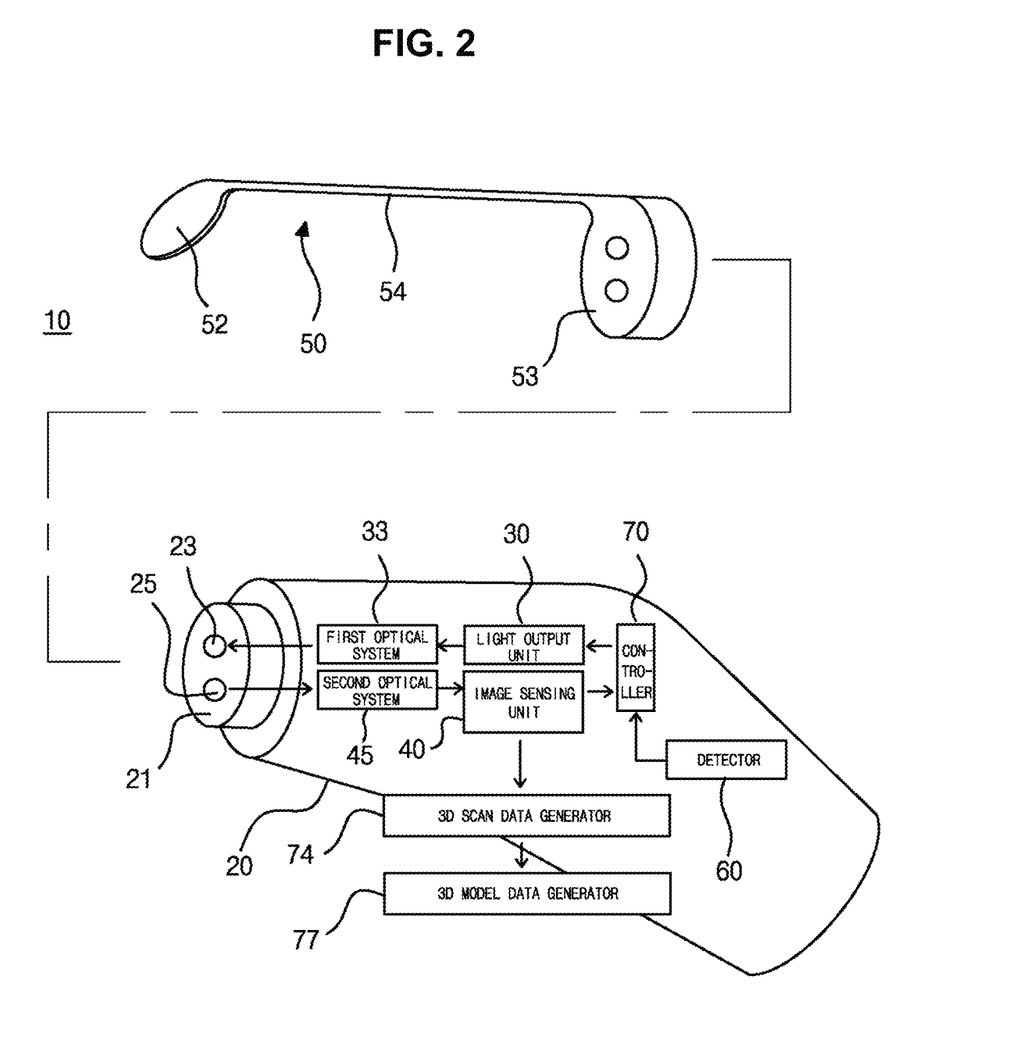
FIG. 2 is a diagram showing the state in which the reflector member is decoupled from the case.

FIGS. 1 and 2 are schematic diagrams of a three-dimensional (3D) intraoral scanner according to an embodiment of the present disclosure, FIG. 1 is a diagram showing the state in which a reflector member is coupled to a case of a 3D intraoral scanner according to an embodiment of the present disclosure, and FIG. 2 is a diagram showing the state in which the reflector member is decoupled from the case.

Referring to FIGS. 1 and 2, a 3D intraoral scanner 10 according to an embodiment of the present disclosure may include a case 20, a light output unit 30, an image sensing unit 40, a reflector member 50, a detector 60, a controller 70, a 3D scan data generator 74, and a 3D model data generator 77.

The case 20 may constitute an outer appearance of the 3D intraoral scanner 10 and may have a front surface 21 including a light outlet 23 for performing an exit function for emitting light output from the light output unit 30 to the outside of the case 20, and a light inlet 25 for performing an entrance function of allowing light reflected from an oral cavity to enter the case 20 again.

The light outlet 23 and the light inlet 25 may be configured in an open form, or may be configured in the form of a transparent plate formed of a transparent material to prevent impurities from entering the case 20 while allowing entering and exiting of light, but the present disclosure is not limited thereto.

The light output unit 30 may be a component that is disposed in the case 20 and outputs predetermined light, for example, patterned light having a pattern or structural light into an oral cavity through the light outlet 23, but the present disclosure is not limited by the arrangement of the light output unit 30 in the case 20, and the 3D intraoral scanner 10 according to an embodiment of the present disclosure may include a first optical system 33 disposed in the case 20 and configured to guide light output from the light output unit 30 to the light outlet 23.

The image sensing unit 40 may use a charged coupled device (CCD) or a complementary metal-oxide semiconductor (CMOS) image sensor as a component disposed in the case 20 and configured to acquire a 2D scan image of the teeth in the oral cavity from the reflected light (light that is emitted through the light outlet 23 and then is reflected from the oral cavity) incident through the light inlet 25, but the present disclosure is not limited by the arrangement of the image sensing unit 40 in the case 20, and the 3D intraoral scanner 10 according to an embodiment of the present disclosure may include a second optical system 45 disposed in the case 20 and configured to guide the reflected light incident through the light inlet 25 to the image sensing unit 40.

The reflector member 50 may be detachably installed on the case 20 and may include a reflector 52 configured to reflect light output through the light outlet 23 into the oral cavity and to reflect the reflected light reflected from the oral cavity to the light inlet 25 when installed in the case 20, and may include a coupler 53 detachably installed on the front surface 21 of the case 20, and an extension 54 that extends from one side of the coupler 53 and has an end with the reflector 52.

The detector 60 may include a light sensor and a button type sensor, which are installed at one side of the front surface 21 of the case 20 and are configured to detect whether the coupler 53 of the reflector member 50 is installed, as a component configured to detect whether the reflector member 50 is installed at the case 20. However, the detector 60 according to the present disclosure may include any component configured to detect whether the reflector member 50 is installed, but the present disclosure is not limited by a detailed configuration of the detector 60.

The controller 70 may be a component for controlling the light output unit 30, the image sensing unit 40, the first optical system 33, and the second optical system 45 and may be configured in the case 20 in the form of a circuit board that is electrically connected to each of the above components.

The 3D scan data generator 74 may generate 3D scan data of the teeth in the oral cavity using the 2D scan image acquired when the reflector member 50 is not installed, and may generate the 3D scan data of the teeth in the oral cavity using the 2D scan image acquired from reflected light reflected by the reflector 52 when the reflector member 50 is installed, as a component configured to generate the 3D scan data of the teeth in the oral cavity using a 2D scan image acquired by the image sensing unit 40.

The 3D model data generator 77 may generate 3D model data of all teeth in the oral cavity by registering 3D scan data generated when the reflector member 50 is not installed, and may register the 3D scan data generated when the reflector member 50 is installed to the 3D model data, as a component configured to generate the 3D model data of all teeth in the oral cavity by registering the 3D scan data generated by the 3D scan data generator 74.

That is, if a 2D scan image that is acquired from the reflected light reflected on the reflector 52 by the image sensing unit 40 may be referred to as a 2D scan image of a narrow area when the reflector member 50 is installed on the case 20, and a 2D scan image that is acquired from the reflected light incident through the light inlet 25 by the image sensing unit 40 is referred to as a 2D scan image of a wide area when the reflector member 50 is not installed on the case 20, the 3D scan data generator 74 may generate 3D scan data of the teeth in the oral cavity using the 2D scan image of the wide area when installation of the reflector member 50 is not detected by the detector 60, and may generate 3D scan data of the teeth in the oral cavity using the 2D scan image of the narrow area when installation of the reflector member 50 is detected by the detector 60.

If 3D scan data of the teeth in the oral cavity, which is generated using the 2D scan image of the wide area by the 3D scan data generator 74, is referred to as 3D scan data of the wide area, and 3D scan data of the teeth in the oral cavity, which is generated using the 2D scan image of the narrow area, is referred to as 3D scan data of the narrow area, the 3D model data generator 77 may generate 3D model data of all teeth in the oral cavity by registering the 3D scan data of the wide area and may register the 3D scan data of the narrow area to the 3D model data.

The 3D intraoral scanner 10 according to an embodiment of the present disclosure as configured above may reduce the number of 3D scan data that needs to be registered in order to generate the 3D model data of all teeth in the oral cavity by generating the 3D model data by registering the 3D scan data generated using the 2D scan image of the wide area, thereby minimizing accumulated errors that occurs when the 3D scan data is registered, and may supplement and fill a missing part of the 3D model data generated using the 2D scan image of the wide area by registering the 3D scan data generated using the 2D scan image of the narrow area to the 3D model data, thereby improving precision of the 3D model data.

The 3D scan data generator 74 and the 3D model data generator 77 may each be embodied by directly installing a functional program, a code, a code segment, etc. for embodying the 3D intraoral scanner 10 according to the present disclosure, or may be embodied in the state in which the functional program, the code, the code segment, etc. for embodying the 3D intraoral scanner 10 according to the present disclosure is stored and executed by a separate computer outside the case 20 of the 3D intraoral scanner 10 through a computer readable recording medium, but the present disclosure is not limited thereto.

Figure 3:
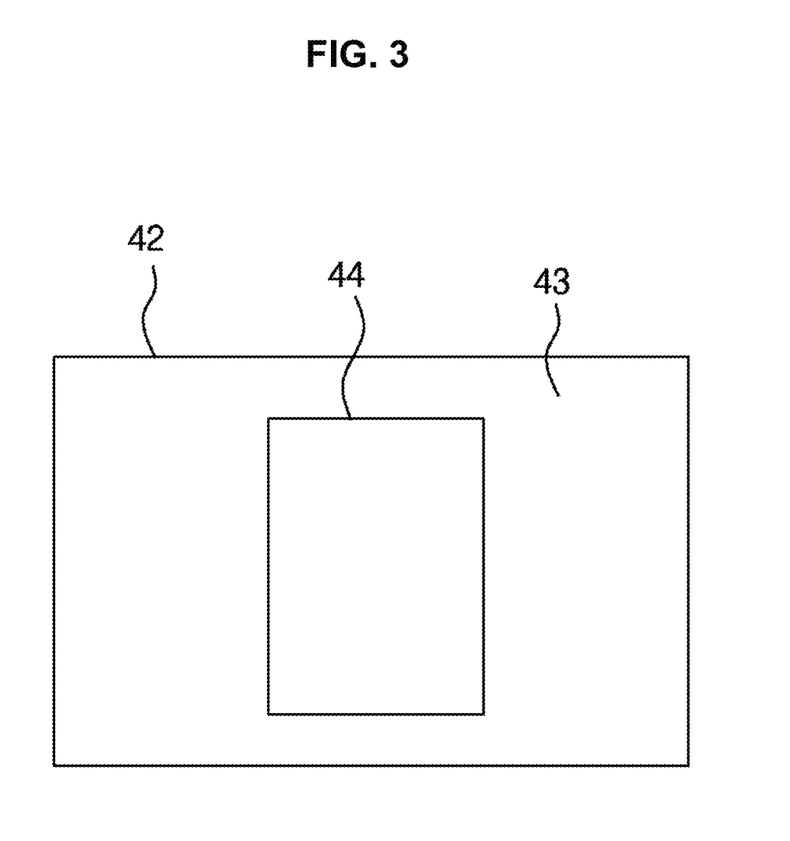
FIG. 3 is a schematic diagram of 2D scan image acquired by an image sensing unit when scan is performed in the state in which the reflector member is installed.

FIG. 3 is a schematic diagram of 2D scan image acquired by an image sensing unit when scan is performed in the state in which the reflector member is installed.

As shown in FIG. 3, when the reflector member 50 is installed on the case 20, 2D scan image 42 that is acquired from entire reflected light incident through the light inlet 25 by the image sensing unit 40 may include 2D scan image 43 acquired from reflected light that is directly incident on the light inlet 25 rather than reflected by the reflector 52 as well as 2D scan image 44 (i.e., the 2D scan image of the narrow area) acquired from the reflected light reflected by the reflector 52.

Here, the 2D scan image 42 that is acquired from entire reflected light incident through the light inlet 25 by the image sensing unit 40 when the reflector member 50 is installed on the case 20 may be 2D scan image that is acquired from entire reflected light incident through the light inlet 25 by the image sensing unit 40 when the reflector member 50 is not installed on the case 20, that is, the 2D scan image 42 of the wide area.

That is, in the 3D intraoral scanner 10 according to an embodiment of the present disclosure, the 2D scan image that is acquired from the entire reflected light incident through the light inlet 25 by the image sensing unit 40 when the reflector member 50 is installed on the case 20 may be the 2D scan image 42 of the wide area including the 2D scan image 44 of the narrow area.

In this case, 3D scan data with respect to the 2D scan image of the narrow area may be generated by selecting only the 2D scan image 44 of the narrow area of the 2D scan image 42 of the wide area that is acquired when the reflector member 50 is installed on the case 20.

Here, the 2D scan image 44 of the narrow area may be selected by recognizing an edge of the 2D scan image 44 of the narrow area.

The 2D scan image 42 of the wide area may include 2D scan image of about two to three teeth, and the 2D scan image 44 of the narrow area may include 2D scan image of about one tooth.

Then, the 3D scan data generator 74 may generate 3D scan data of about two to three teeth using the 2D scan image 42 of the wide area when installation of the reflector member 50 is not detected by the detector 60, and may generate 3D scan data of about one tooth using the 2D scan image 44 of the narrow area when installation of the reflector member 50 is detected by the detector 60.

In this case, the 3D model data generator 77 may minimize accumulated errors occurring when the 3D scan data are registered by registering the 3D scan data of the wide area to generate 3D model data about all teeth in the oral cavity, and may supplement and fill a missing part of the 3D model data generated using the 3D scan data of the wide area by registering the 3D scan data of the narrow area to the 3D model data, thereby improving resolution of the 3D model data.

Figure 4:
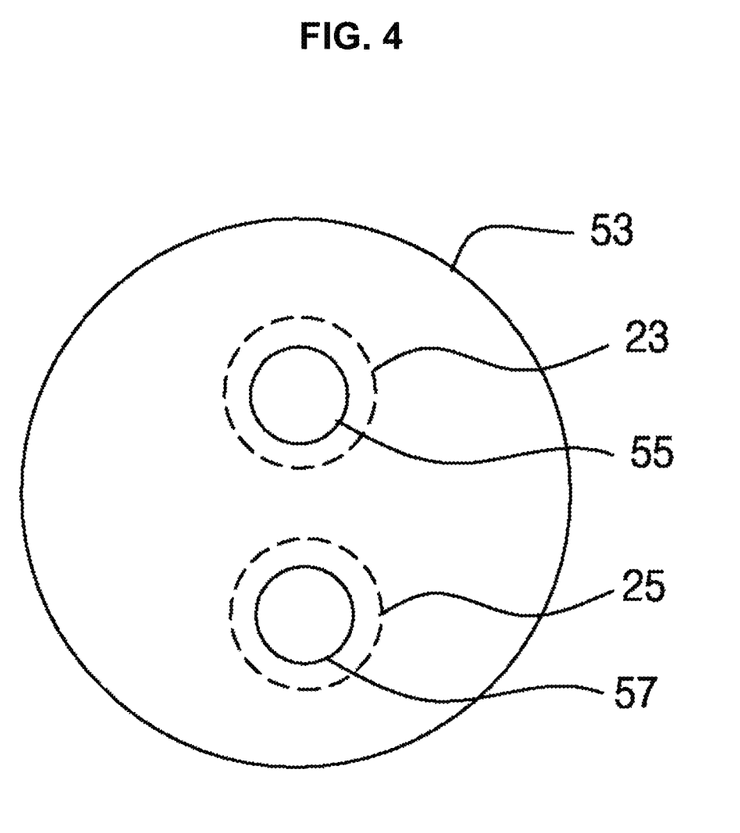
FIG. 4 is a schematic plan view showing the state in which a coupler of a reflector member is installed on a front surface of a case according to an embodiment of the present disclosure.
Figure 5:
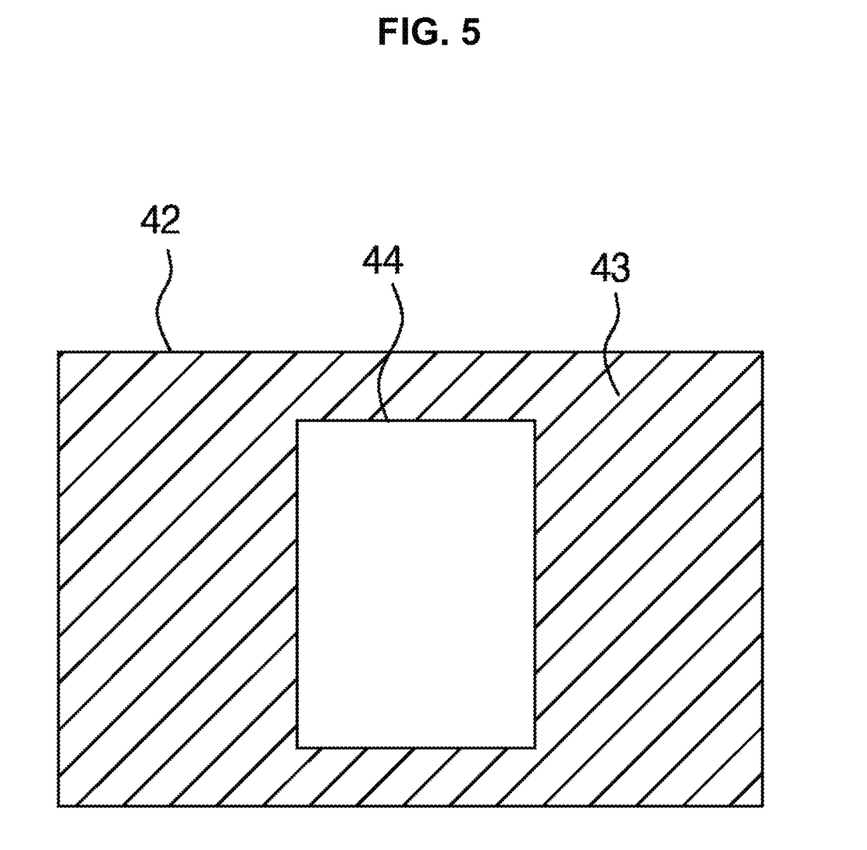
FIG. 5 is a schematic diagram of 2D scan image acquired by an image sensing unit when the reflector member shown in FIG. 4 is installed on a case.

FIG. 4 is a schematic plan view showing the state in which a coupler of a reflector member is installed on a front surface of a case according to an embodiment of the present disclosure. FIG. 5 is a schematic diagram of 2D scan image acquired by an image sensing unit when the reflector member shown in FIG. 4 is installed on a case.

First, referring to FIG. 4, the reflector member 50 according to an embodiment of the present disclosure may further include at least one of a primary light unit 55 and a secondary light unit 57.

The primary light unit 55 may have an opening a transparent part having a smaller size than the light outlet 23 and configured to hide a portion of the light outlet 23 when the coupler 53 of the reflector member 50 is installed on the front surface 21 of the case 20 in order to output only light output to the reflector 52 of light output through the light outlet 23.

The secondary light unit 57 may have an opening a transparent part having a smaller size than the light inlet 25 and configured to hide a portion of the light inlet 25 when the coupler 53 of the reflector member 50 is installed on the front surface 21 of the case 20 in order to allow only reflected light reflected by the reflector 52 of the reflected light incident through the light inlet 25 to be incident.

As shown in FIG. 5, when the reflector member 50 further includes at least one of the primary light unit 55 and the secondary light unit 57, the 2D scan image 42 (that is, the 2D data of the wide area) acquired by the image sensing unit 40 may make only the 2D scan image 44 (that is, the scan image of the narrow area) acquired from the reflected light reflected by the reflector 52 appear light, and may make the 2D scan image 43 of an area except for the 2D scan image 44 of the narrow area of the 2D scan image 42 of the wide area appear dark.

Thus, the 3D scan data generator 74 may generate only 3D scan data of the 2D scan image 44 of the narrow area by easily selecting only the 2D scan image 44 of the narrow area of the 2D scan image 42 of the wide area that is acquired when the reflector member 50 is installed on the case 20.

The reflector member 50 may be rotatably installed on the case 20.

Then, when the upper and lower teeth in the oral cavity are scanned, it may be convenient to scan the upper or lower teeth while rotating the reflector member 50 in the state in which the reflector member 50 is installed on the case 20.

When installation of the reflector member 50 is detected by the detector 60, the controller 70 may control the light output unit 30 to output light output through the light outlet 23 only to the reflector 52.

For example, in the case of a digital light processing (DLP) projector including a digital mirror device (DVD) chipset having a micro mirror for adjusting an angle of reflection of light output from the light output unit 30, the controller 70 may control the micro mirror to output light output through the light outlet 23 only to the reflector 52 when installation of the reflector member 50 is detected by the detector 60.

Figure 6:
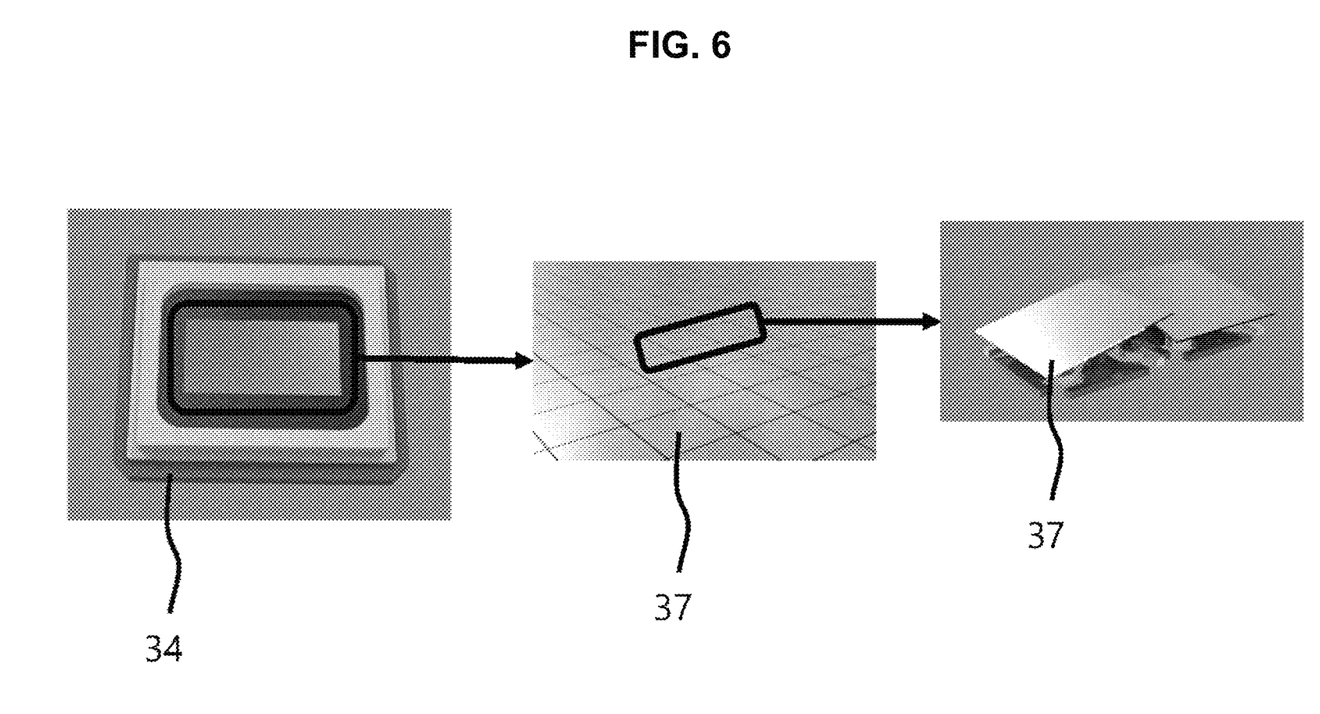
FIG. 6 is a schematic diagram of a digital mirror device (DMD) chipset and a micro mirror of a DLP projector as one type of a light output unit according to an embodiment of the present disclosure.

FIG. 6 is a schematic diagram of a DMD chipset and a micro mirror of a DLP projector as one type of a light output unit according to an embodiment of the present disclosure.

As shown in FIG. 6, the DLP projector may include a MID chipset 34, and numerous micro mirrors 37 for adjusting an angle of reflection of light output from the DLP projector may be arranged on a surface of the DMD chipset 34. Here, one micro mirror 37 may correspond to one pixel.

In this case, the controller 70 according to an embodiment of the present disclosure may control the micro mirror 37 to output light output through the light outlet 23 only to the reflector 52 when installation of the reflector member 50 is detected by the detector 60.

Then, as shown in FIG. 5, like in the case in which the reflector member 50 further includes at least one of the primary light unit 55 and the secondary light unit 57, the 2D scan image 42 (that is, the 2D scan image of the wide area) acquired by the image sensing unit 40 may make only the 2D scan image 44 (that is, the scan image of the narrow area) acquired from the reflected light reflected by the reflector 52 appear light, and may make the 2D scan image 43 of an area except for the 2D scan image 44 of the narrow area of the 2D scan image 42 of the wide area appear dark.

In another example, in the case of a liquid crystal display (LCD) projector in which the light output unit 30 includes a plurality of pixels (liquid crystal) only when current flows in the light output unit 30, the controller 70 may control on/off of current of each pixel to output the light output through the light outlet 23 only to the reflector 52 when installation of the reflector member 50 is detected by the detector 60.

Hereinafter, an oral cavity scanning method using the 3D intraoral scanner 10 according to an embodiment of the present disclosure will be described in detail with reference to the drawings.

Figure 7:
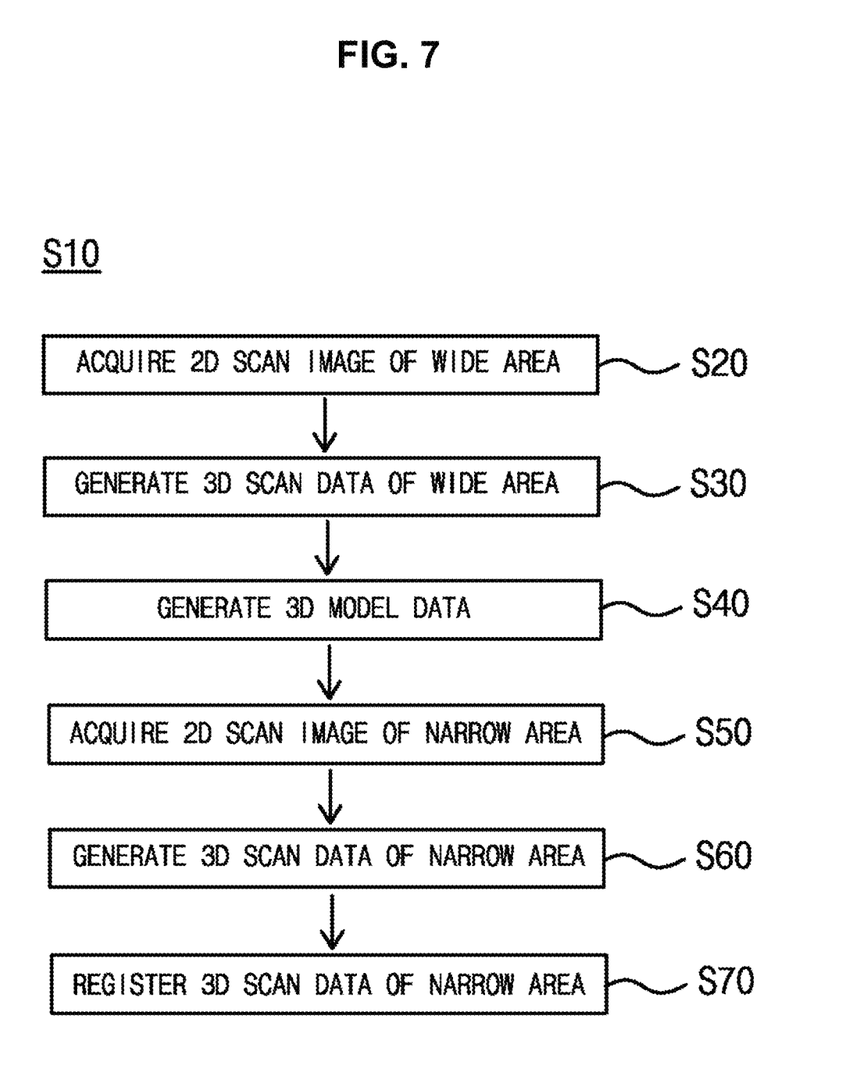
FIG. 7 is a schematic flowchart of an oral cavity scanning method using a 3D intraoral scanner according to an embodiment of the present disclosure.

FIG. 7 is a schematic flowchart of an oral cavity scanning method using a 3D intraoral scanner according to an embodiment of the present disclosure.

Referring to FIG. 7, an oral cavity scanning method S10 using the 3D intraoral scanner 10 according to an embodiment of the present disclosure may include operation S20 of acquiring 2D scan image of a wide area, operation S30 of generating 3D scan data of a wide area, operation S40 of generating 3D model data, operation S50 of acquiring 2D scan image of a narrow area, operation S60 of acquiring 3D scan data of a narrow area, and operation S70 of registering a 3D scan image of a narrow area.

The operation S20 of acquiring 2D scan image of a wide area may an operation of acquiring the 2D scan image 42 of the wide area in the state in which the reflector member 50 is not installed on the case 20.

The operation S30 of generating 3D scan data of a wide area may be an operation of generating the 3D scan data of the wide area of the teeth in the oral cavity using the acquired 2D scan image 42 of the wide area.

The operation S40 of generating 3D model data may be an operation of generating the 3D model data of the all teeth in the oral cavity by registering the 3D scan data of the wide area.

The operation S50 of acquiring 2D scan image of a narrow area may be an operation of acquiring the 2D scan image 44 of the narrow area in the state in which the reflector member 50 is installed on the case 20.

The operation S60 of acquiring 3D scan data of a narrow area may be an operation of generating the 3D scan data of the narrow area of the teeth in the oral cavity using the acquired 2D scan image 44 of the narrow area.

The operation S70 of registering a 3D scan image of a narrow area may be an operation of registering the 3D scan data of the narrow area to the 3D model data.

In the oral cavity scanning method S10 according to an embodiment of the present disclosure, the 2D scan image that is acquired from the entire reflected light incident through the light inlet 25 by the image sensing unit 40 when the reflector member 50 is installed on the case 20 may be the 2D scan image 42 of the wide area including the 2D scan image 44 of the narrow area.

In this case, the operation S50 of acquiring 2D scan image of a narrow area may include an operation of acquiring the 2D scan image 42 of the wide area in the state in which the reflector member 50 is installed on the case 20 and an operation of selecting the 2D scan image 44 of the narrow area from the 2D scan image 42 of the wide area.

Figure 8:
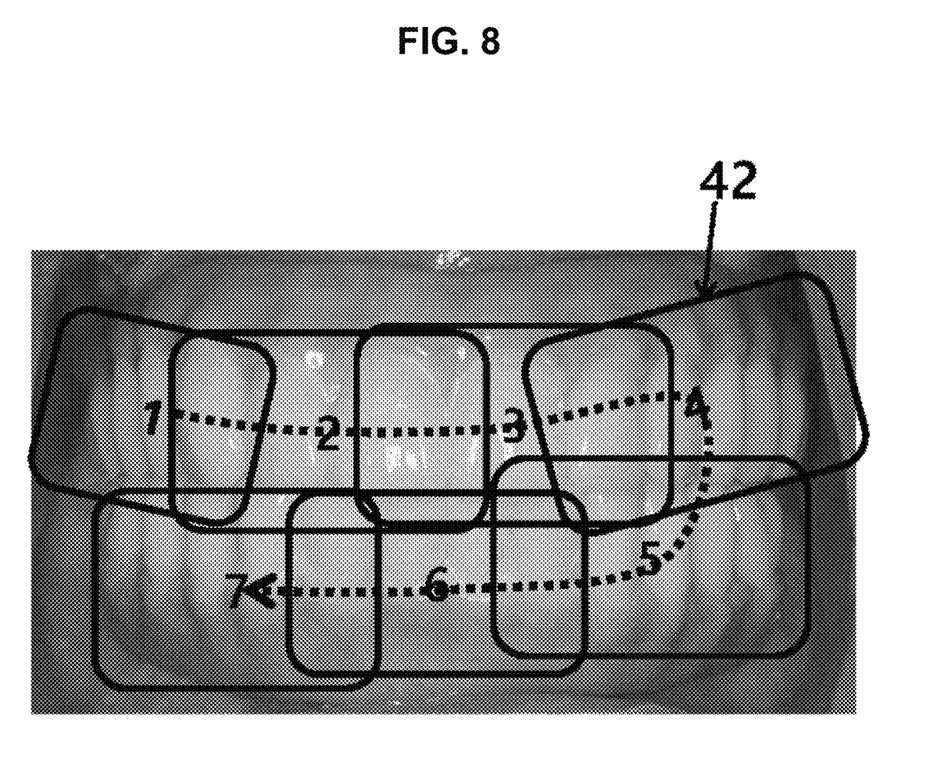
FIG. 8 is a schematic diagram showing a scan region in an oral cavity in the case of scanning without installation of a reflector member.
Figure 9:
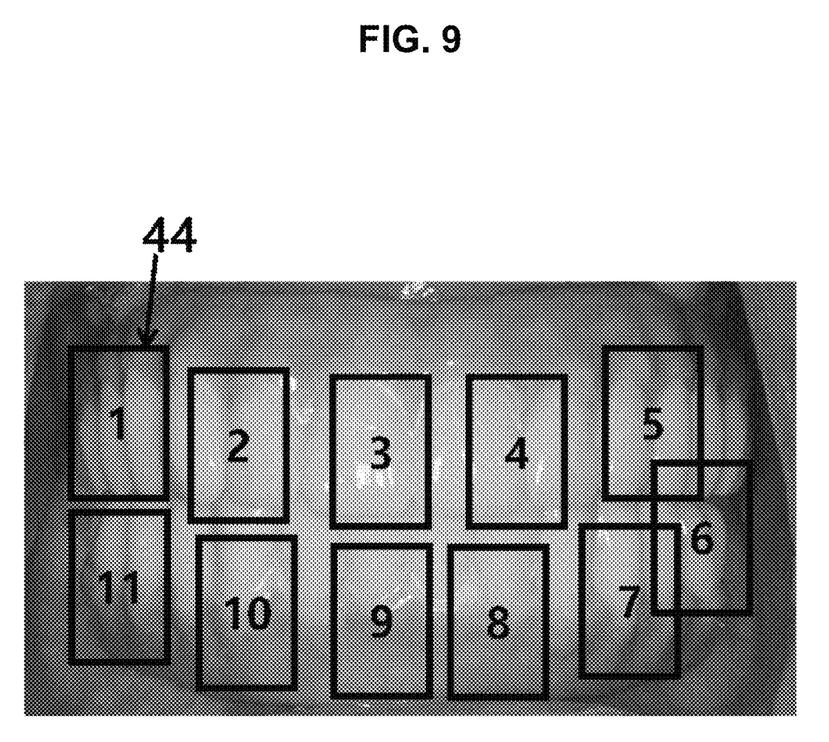
FIG. 9 is a schematic diagram showing a scan region in an oral cavity in the case of scanning with installation of a reflector member.

FIG. 8 is a schematic diagram showing a scan region in an oral cavity in the case of scanning without installation of a reflector member. FIG. 9 is a schematic diagram showing a scan region in an oral cavity in the case of scanning with installation of a reflector member.

FIG. 8 shows a scan region 42 (a region in which about two to three teeth are scanned at once) in the oral cavity in the case of scanning at once without installation of the reflector member 50, and in this case, the 2D scan image that is acquired from the scan region 42 by the image sensing unit 40 may be the 2D scan image 42 of the wide area.

FIG. 9 shows a scan region 44 (a region in which about one tooth is scanned at once) in the oral cavity in the case of scanning at once with installation of the reflector member 50, and in this case, the 2D scan image that is acquired from the scan region 44 by the image sensing unit 40 may be the 2D scan image 44 of the narrow area.

As seen from FIG. 8, 3D model data of all the teeth in the oral cavity using the 2D scan image 42 of the wide area may be generated through scanning about seven times, but as seen from FIG. 9, when 3D model data is generated using the 2D scan image 44 of the narrow area is generated, it may be impossible to generate 3D model data of all the teeth in the oral cavity through scanning about 11 times.

Accordingly, by virtue of the 3D intraoral scanner 10 and the oral cavity scanning method S10 using the same according to an embodiment of the present disclosure, the 3D model data of all the teeth in the oral cavity may be generated using the 2D scan image 42 of the wide area (the 2D scan image acquired through scanning without installation of the reflector member 50), and accordingly, a number of times of registering 3D scan data may be reduced compared with the case in which the 3D model data of all the teeth in the oral cavity is generated using the 2D scan image 44 of the narrow area (2D scan image acquired through scanning with installation of the reflector member 50), and accordingly, accumulated errors occurring when 3D scan data is registered may be minimized.

An example of the procedure of generating the 3D model data of all the teeth in the oral cavity is now described with reference to FIG. 8, and scanning may be performed on overlapping regions in a direction indicated by an arrow of FIG. 8, that is, a direction toward #7 from #1 of the scan region 42 to generate 3D scan data of the respective regions, and then the seven generated 3D scan data may be registered to generate the 3D model data of all the teeth in the oral cavity.

In this case, as shown in FIG. 9, with respect to a part that requires high precision of the generated 3D model data of all the teeth of in the oral cavity, for example, a part between the teeth or a part that needs to be directly treated, 3D scan data may be generated using the 2D scan image 44 of the narrow area acquired through scanning with installation of the reflector member 50 and the generated 3D scan data may be registered to the 3D model data of all the teeth in the oral cavity, and thus a missing part of the 3D model data generated using the 2D scan image 42 of the wide area may be supplemented and filled, thereby improving precision of the 3D model data.

As described above, the present disclosure relates to a 3D intraoral scanner and an oral cavity scanning method using the same for reducing a registration error occurring in a procedure of generating 3D model data of all the teeth in the oral cavity, and embodiments of the present disclosure may be modified in various forms. Accordingly, the present disclosure is not limited by the embodiments disclosed herein, and all forms that can be changed by one of ordinary skill in the art to which the present disclosure pertains will fall within the scope of the present disclosure.

What is claimed is:
1. A three-dimensional (3D) intraoral scanner comprising:
a case having a cylindrical front portion having a front surface including a light outlet and a light inlet;
a light output unit disposed in the case and configured to output light into an oral cavity through the light outlet;
a reflector member detachably installed on the case and comprising a reflector configured to reflect light output through the light outlet when installed in the case;
an image sensing unit disposed in the case to receive light through the light inlet, wherein the image sensing unit is configured to acquire 2D wide scan images of teeth in the oral cavity in a wide scan mode and to further acquire 2D narrow scan images of the teeth in a narrow scan mode; and a processor configured to generate 3D wide scan data of the teeth using the 2D wide scan images and to generate 3D narrow scan data of the teeth using the 2D narrow scan images;

wherein the processor is further configured to generate 3D model data for all of the teeth by registering the 3D wide scan data of the teeth and to register the 3D narrow scan data to the 3D model data generated in the wide scan mode.

2. The 3D intraoral scanner of claim 1, further comprising:

a detector configured to detect whether the reflector member is installed on the case;

wherein the image sensing unit operates in the wide scan mode when installation of the reflector member is not detected by the detector and the image sensing unit operates in the narrow scan mode when the installation of the reflector member is detected by the detector.

3. The 3D intraoral scanner of claim 1, further comprising:

a detector configured to detect whether the reflector member is installed on the case; and a controller configured to control the light output unit to output light output through the light outlet only to the reflector when installation of the reflector member is detected by the detector.

4. The 3D intraoral scanner of claim 1, wherein the reflector member includes at least one of a primary light unit hiding a part of the light outlet to output only the light output to the reflector of the light output through the light outlet when installed on the case, and a secondary light unit hiding a part of the light inlet to allow only reflected light reflected by the reflector of the reflected light incident through the light inlet to be incident.

5. The 3D intraoral scanner of claim 1, wherein the reflector member is rotatably installed on the case.

6. The 3D intraoral scanner of claim 1, wherein the reflector member includes a coupler detachably installed on the front surface of the case, and an extension extending from one side of the coupler and having an end with the reflector.

7. An oral cavity scanning method using a three-dimensional (3D) intraoral scanner including a case having a front surface including a light outlet and a light inlet, a light output unit configured to output light into an oral cavity through the light outlet, an image sensing unit configured to acquire 2D scan image of teeth in the oral cavity from reflected light incident through the light inlet, and a reflector member detachably installed on the case and including a reflector configured to reflect light output through the light outlet into the oral cavity and to reflect reflected light reflected from the oral cavity to the light inlet when installed in the case, the method comprising:

acquiring, by the image sensing unit, 2D wide scan images of the teeth in a wide scan mode;

generating, by a processor, 3D wide scan data of the teeth using the 2D wide scan images;

generating, by the processor, 3D model data for all of the teeth by registering the 3D wide scan data of the teeth;

acquiring, by the image sensing unit, 2D narrow scan images of the teeth in a narrow scan mode;

generating, by the processor, 3D narrow scan data of the teeth using the 2D narrow scan images; and registering, by the processor, the 3D narrow scan data to the 3D model data generated in the wide scan mode.

8. The 3D intraoral scanner of claim 1, wherein the reflector member is not installed on the case in the wide scan mode.

9. The 3D intraoral scanner of claim 1, wherein the reflector member is installed on the case in the narrow scan mode.

10. The 3D intraoral scanner of claim 1, wherein the reflector member further comprises:

a coupler detachably coupled to the cylindrical front portion of the case, the coupler having first and second openings corresponding to the light outlet and the light inlet, respectively, wherein diameters of the first and second openings are less than diameters of the light outlet and the light inlet, respectively; and an extension having a front end connected to the reflector and a rear end connected to an edge portion of a front surface of the coupler.

11. The oral cavity scanning method of claim 7, wherein the reflector member is not installed on the case in the wide scan mode.

12. The oral cavity scanning method of claim 7, wherein the reflector member is installed on the case in the narrow scan mode.

* * * * *